United States Patent
Jackson et al.

(10) Patent No.: US 9,636,146 B2
(45) Date of Patent: *May 2, 2017

(54) MULTI-START CLOSURES FOR OPEN IMPLANTS

(71) Applicant: Roger P. Jackson, Prairie Village, KS (US)

(72) Inventors: Roger P Jackson, Prairie Village, KS (US); James L Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 9 days.

This patent is subject to a terminal disclaimer.

(21) Appl. No.: 14/566,356

(22) Filed: Dec. 10, 2014

(65) Prior Publication Data
US 2015/0094770 A1 Apr. 2, 2015

Related U.S. Application Data

(63) Continuation of application No. 13/694,849, filed on Jan. 10, 2013, now Pat. No. 8,911,479.

(60) Provisional application No. 61/631,746, filed on Jan. 10, 2012, provisional application No. 61/634,361, filed on Feb. 28, 2012.

(51) Int. Cl.
*A61B 17/70* (2006.01)
*A61B 17/86* (2006.01)

(52) U.S. Cl.
CPC ...... *A61B 17/7032* (2013.01); *A61B 17/7035* (2013.01); *A61B 17/8665* (2013.01)

(58) Field of Classification Search
CPC ............ A61B 17/7032; A61B 17/7035; A61B 17/8665

USPC ....... 606/246, 264–273, 275, 278, 279, 305, 606/306, 308, 315, 316; 403/362; 411/393
See application file for complete search history.

(56) References Cited

U.S. PATENT DOCUMENTS

| 154,864 A | 9/1874 | Harvey |
| 791,548 A | 6/1905 | Fischer |
| 1,300,275 A | 4/1919 | Johnson |

(Continued)

FOREIGN PATENT DOCUMENTS

| AU | 2012203959 | 8/2012 |
| DE | 373809 | 4/1923 |

(Continued)

OTHER PUBLICATIONS

Brochure of Tyco/Healthcare/Surgical Dynamics on Spiral Radius 90D, Publication Date: Sep. 2001, pp. 1-8.

(Continued)

*Primary Examiner* — Pedro Philogene
*Assistant Examiner* — David C Comstock
(74) *Attorney, Agent, or Firm* — Polsinelli PC

(57) ABSTRACT

An open implant closure structure includes a helically wound guide and advancement structure having at least two helically wound forms thereon providing a multi-start closing mechanism for use between spaced arms of a cooperating open medical implant having mating helically wound structure thereon. Illustrated structures include interlocking flange forms, v-threads, square threads, reverse angle threads and buttress threads and receivers with break-off extensions and cooperating tooling.

30 Claims, 7 Drawing Sheets

(56) References Cited

U.S. PATENT DOCUMENTS

| | | |
|---|---|---|
| 1,330,673 A | 2/1920 | Anderson |
| 1,472,464 A | 10/1923 | Ellison |
| 2,083,092 A | 6/1937 | Richer |
| 2,201,087 A | 5/1940 | Hallowell |
| 2,239,352 A | 4/1941 | Cherry |
| 2,243,717 A | 5/1941 | Moreira |
| 2,295,314 A | 9/1942 | Whitney |
| 2,346,346 A | 4/1944 | Anderson |
| 2,362,999 A | 11/1944 | Elmer |
| 2,445,978 A | 7/1948 | Stellin |
| 2,531,892 A | 11/1950 | Reese |
| 2,532,815 A | 12/1950 | Kindsvatter et al. |
| 2,537,029 A | 1/1951 | Cambern |
| 2,553,337 A | 5/1951 | Shafer |
| 2,778,265 A | 1/1957 | Brown |
| 2,813,450 A | 11/1957 | Dzus |
| 2,877,681 A | 3/1959 | Brown |
| 2,927,332 A | 3/1960 | Moore |
| 2,969,250 A | 1/1961 | Kull |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,444,775 A | 5/1969 | Hills |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Gryctko |
| 3,989,284 A | 11/1976 | Blose |
| 3,997,138 A | 12/1976 | Crock et al. |
| 4,013,071 A | 3/1977 | Rosenberg |
| 4,033,139 A | 7/1977 | Frederick |
| 4,041,939 A | 8/1977 | Hall |
| 4,103,422 A | 8/1978 | Weiss et al. |
| 4,190,091 A | 2/1980 | Colognori |
| 4,269,246 A | 5/1981 | Larson et al. |
| 4,323,326 A | 4/1982 | Okada et al. |
| 4,347,845 A | 9/1982 | Mayfield |
| 4,369,769 A | 1/1983 | Edwards |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen |
| 4,577,448 A | 3/1986 | Howorth |
| 4,600,224 A | 7/1986 | Blose |
| 4,600,225 A | 7/1986 | Blose |
| 4,641,636 A | 2/1987 | Cotrel |
| 4,653,481 A | 3/1987 | Howland et al. |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee et al. |
| 4,877,020 A | 10/1989 | Vich |
| 4,887,596 A | 12/1989 | Sherman |
| 4,917,606 A | 4/1990 | Miller |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,042,982 A | 8/1991 | Harms et al. |
| 5,056,492 A | 10/1991 | Banse |
| 5,067,428 A | 11/1991 | Dickerson et al. |
| 5,067,955 A | 11/1991 | Cotrel |
| 5,073,074 A | 12/1991 | Corrigan et al. |
| 5,084,048 A | 1/1992 | Jacob et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,201,734 A | 4/1993 | Cozad et al. |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,263,953 A | 11/1993 | Bagby |
| 5,275,601 A | 1/1994 | Gogolewski et al. |
| 5,282,707 A | 2/1994 | Palm |
| 5,282,862 A | 2/1994 | Baker et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,211 A | 2/1995 | Saadatmanesh et al. |
| 5,387,212 A | 2/1995 | Yuan et al. |
| 5,395,371 A | 3/1995 | Miller et al. |
| 5,409,488 A | 4/1995 | Ulrich |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,434,001 A | 7/1995 | Yamada et al. |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,501,684 A | 3/1996 | Schlapfer et al. |
| 5,505,731 A | 4/1996 | Tornier |
| 5,507,745 A | 4/1996 | Logroscino et al. |
| 5,507,747 A | 4/1996 | Yuan et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,549,608 A | 8/1996 | Errico et al. |
| 5,554,157 A | 9/1996 | Errico et al. |
| 5,562,660 A | 10/1996 | Grob |

(56) References Cited

U.S. PATENT DOCUMENTS

| | | |
|---|---|---|
| 5,562,663 A | 10/1996 | Wisnewski et al. |
| 5,569,247 A | 10/1996 | Morrison |
| 5,569,251 A | 10/1996 | Baker et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,605,458 A | 2/1997 | Bailey et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,662,653 A | 9/1997 | Songer et al. |
| 5,667,508 A | 9/1997 | Errico et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann |
| 5,676,665 A | 10/1997 | Bryan |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,702,393 A | 12/1997 | Pfaifer |
| 5,711,709 A | 1/1998 | McCoy |
| 5,713,705 A | 2/1998 | Grunbichler |
| 5,713,898 A | 2/1998 | Stuecker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,351 A | 3/1999 | Viart |
| 5,882,350 A | 3/1999 | Ralph et al. |
| 5,902,303 A | 5/1999 | Eckhof et al. |
| RE36,221 E | 6/1999 | Breard et al. |
| 5,910,141 A | 6/1999 | Morrison et al. |
| 5,910,142 A | 6/1999 | Tatar |
| 5,928,236 A | 7/1999 | Augagneur et al. |
| 5,938,663 A | 8/1999 | Petreto |
| 5,941,880 A | 8/1999 | Errico et al. |
| 5,944,465 A | 8/1999 | Janitzki |
| 5,951,553 A | 9/1999 | Betz et al. |
| 5,961,517 A | 10/1999 | Biedermann et al. |
| 5,964,760 A | 10/1999 | Richelsoph |
| 5,964,767 A | 10/1999 | Tapia et al. |
| 5,997,539 A | 12/1999 | Errico et al. |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,056,753 A | 5/2000 | Jackson |
| 6,063,088 A | 5/2000 | Winslow |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,117,137 A | 9/2000 | Halm et al. |
| 6,129,763 A | 10/2000 | Chauvin et al. |
| 6,132,431 A | 10/2000 | Nilsson et al. |
| 6,136,002 A | 10/2000 | Shih et al. |
| 6,136,003 A | 10/2000 | Hoeck et al. |
| 6,139,549 A | 10/2000 | Keller |
| 6,143,032 A | 11/2000 | Schafer et al. |
| 6,146,383 A | 11/2000 | Studer et al. |
| 6,149,533 A | 11/2000 | Finn |
| 6,162,223 A | 12/2000 | Orsak et al. |
| 6,168,597 B1 | 1/2001 | Biedermann et al. |
| 6,183,472 B1 | 2/2001 | Lutz |
| 6,186,718 B1 | 2/2001 | Fogard |
| 6,193,719 B1 | 2/2001 | Gournay et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,241,731 B1 | 6/2001 | Fiz |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,280,445 B1 | 8/2001 | Morrison et al. |
| 6,287,308 B1 | 9/2001 | Betz et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| RE37,665 E | 4/2002 | Ralph et al. |
| 6,368,321 B1 | 4/2002 | Jackson |
| 6,371,957 B1 | 4/2002 | Amrein |
| 6,379,356 B1 | 4/2002 | Jackson |
| 6,402,757 B1 | 6/2002 | Moore et al. |
| 6,440,133 B1 | 8/2002 | Beale et al. |
| 6,443,956 B1 | 9/2002 | Ray |
| 6,467,958 B1 | 10/2002 | Sasaki et al. |
| 6,471,703 B1 | 10/2002 | Ashman |
| 6,478,797 B1 | 11/2002 | Paul |
| 6,478,798 B1 | 11/2002 | Howland |
| 6,485,491 B1 | 11/2002 | Farris et al. |
| 6,485,492 B1 | 11/2002 | Halm et al. |
| 6,485,494 B1 | 11/2002 | Haider |
| 6,520,962 B1 | 2/2003 | Taylor et al. |
| 6,527,804 B1 | 3/2003 | Gauchet et al. |
| 6,533,786 B1 | 3/2003 | Needham et al. |
| 6,554,831 B1 | 4/2003 | Rivard et al. |
| 6,554,834 B1 | 4/2003 | Crozet et al. |
| 6,562,040 B1 | 5/2003 | Wagner |
| 6,565,565 B1 | 5/2003 | Yuan et al. |
| 6,565,567 B1 | 5/2003 | Haider |
| 6,595,992 B1 | 7/2003 | Wagner et al. |
| 6,602,255 B1 | 8/2003 | Campbell et al. |

(56) References Cited

U.S. PATENT DOCUMENTS

| | | |
|---|---|---|
| 6,613,050 B1 | 9/2003 | Wagner et al. |
| 6,616,667 B1 | 9/2003 | Steiger et al. |
| 6,648,885 B1 | 11/2003 | Friesem |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,663,632 B1 | 12/2003 | Frigg |
| 6,673,073 B1 | 1/2004 | Schaefer |
| 6,676,661 B1 | 1/2004 | Benlloch et al. |
| 6,712,818 B1 | 3/2004 | Michelson |
| 6,716,214 B1 | 4/2004 | Jackson |
| 6,743,231 B1 | 6/2004 | Gray et al. |
| 6,755,829 B1 | 6/2004 | Bono et al. |
| 6,778,861 B1 | 8/2004 | Liebrecht et al. |
| 6,835,196 B2 | 12/2004 | Biedermann et al. |
| 6,872,208 B1 | 3/2005 | McBride et al. |
| 6,896,677 B1 | 5/2005 | Lin |
| 7,001,389 B1 | 2/2006 | Navarro et al. |
| RE39,035 E | 3/2006 | Finn et al. |
| RE39,089 E | 5/2006 | Ralph et al. |
| 7,081,116 B1 | 7/2006 | Carly |
| 7,179,261 B2 | 2/2007 | Sicvol et al. |
| 7,625,394 B2 | 12/2009 | Molz, IV et al. |
| 7,686,833 B1 | 3/2010 | Muhanna et al. |
| 7,766,943 B1 | 8/2010 | Fallin et al. |
| 7,833,251 B1 | 11/2010 | Ahlgren et al. |
| 7,862,587 B2 | 1/2011 | Gordon et al. |
| 7,947,065 B2 | 5/2011 | Hammill, Sr. et al. |
| 7,972,364 B2 | 7/2011 | Biedermann et al. |
| 8,043,340 B1 | 10/2011 | Law |
| 8,092,499 B1 | 1/2012 | Roth |
| 8,114,133 B2 | 2/2012 | Logan |
| 8,114,134 B2 | 2/2012 | Winslow et al. |
| 8,133,262 B2 | 3/2012 | Whipple |
| 8,167,914 B1 | 5/2012 | Hunt et al. |
| 8,197,517 B1 | 6/2012 | Lab et al. |
| 8,206,422 B2 | 6/2012 | Hestad et al. |
| 8,211,110 B1 | 7/2012 | Corin et al. |
| 8,236,035 B1 | 8/2012 | Bedor |
| 8,388,659 B1 | 3/2013 | Lab et al. |
| 8,394,133 B2 | 3/2013 | Jackson |
| 8,439,922 B1 | 5/2013 | Arnold et al. |
| 8,439,924 B1 | 5/2013 | McBride et al. |
| 8,444,681 B2 | 5/2013 | Jackson et al. |
| 8,470,009 B1 | 6/2013 | Rezach |
| 8,911,479 B2 * | 12/2014 | Jackson ............ A61B 17/7035 606/278 |
| 2001/0007941 A1 | 7/2001 | Steiner et al. |
| 2001/0010000 A1 | 7/2001 | Gertzbein et al. |
| 2001/0011172 A1 | 8/2001 | Orbay et al. |
| 2001/0012937 A1 | 8/2001 | Schaffler-Wachter et al. |
| 2001/0023350 A1 | 9/2001 | Choi |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2001/0052438 A1 | 12/2001 | Spencer |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0068975 A1 | 6/2002 | Teitelbaum et al. |
| 2002/0072750 A1 | 6/2002 | Jackson |
| 2002/0072751 A1 | 6/2002 | Jackson |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0095153 A1 | 7/2002 | Jones et al. |
| 2002/0095154 A1 | 7/2002 | Atkinson et al. |
| 2002/0095881 A1 | 7/2002 | Shreiner |
| 2002/0103487 A1 | 8/2002 | Errico et al. |
| 2002/0111627 A1 | 8/2002 | Vincent-Prestigiacomo |
| 2002/0116001 A1 | 8/2002 | Schafer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143328 A1 | 10/2002 | Shluzas et al. |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173791 A1 | 11/2002 | Howland |
| 2002/0183747 A1 | 12/2002 | Jao et al. |
| 2002/0198526 A1 | 12/2002 | Shaolian et al. |
| 2003/0004519 A1 | 1/2003 | Torode et al. |
| 2003/0023243 A1 | 1/2003 | Biedermann et al. |
| 2003/0028191 A1 | 2/2003 | Shluzas |
| 2003/0032957 A1 | 2/2003 | McKinley |
| 2003/0055426 A1 | 3/2003 | Carbone et al. |
| 2003/0055427 A1 | 3/2003 | Graf |
| 2003/0060826 A1 | 3/2003 | Foley et al. |
| 2003/0073995 A1 | 4/2003 | Reed |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0139745 A1 | 7/2003 | Ashman |
| 2003/0149430 A1 | 8/2003 | Ferrante et al. |
| 2003/0149431 A1 | 8/2003 | Varieur |
| 2003/0149432 A1 | 8/2003 | Frigg et al. |
| 2003/0149435 A1 | 8/2003 | Baynham et al. |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176863 A1 | 9/2003 | Ueyama et al. |
| 2003/0181913 A1 | 9/2003 | Lieberman |
| 2003/0187433 A1 | 10/2003 | Lin |
| 2003/0187434 A1 | 10/2003 | Lin |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0208204 A1 | 11/2003 | Bailey et al. |

(56) References Cited

U.S. PATENT DOCUMENTS

| | | |
|---|---|---|
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0006342 A1 | 1/2004 | Altarac et al. |
| 2004/0039383 A1 | 2/2004 | Jackson |
| 2004/0039384 A1 | 2/2004 | Boehm, Jr. et al. |
| 2004/0039385 A1 | 2/2004 | Mazda et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0122442 A1 | 6/2004 | Lewis |
| 2004/0127897 A1 | 7/2004 | Freid et al. |
| 2004/0127904 A1 | 7/2004 | Konieczynski et al. |
| 2004/0133207 A1 | 7/2004 | Abdou |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0153068 A1 | 8/2004 | Janowski et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167523 A1 | 8/2004 | Jackson |
| 2004/0167525 A1 | 8/2004 | Jackson |
| 2004/0172025 A1 | 9/2004 | Drewry et al. |
| 2004/0172031 A1 | 9/2004 | Rubecamp et al. |
| 2004/0172032 A1 | 9/2004 | Jackson |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0210227 A1 | 10/2004 | Trail et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236330 A1 | 11/2004 | Purcell et al. |
| 2004/0249378 A1 | 12/2004 | Saint Martin et al. |
| 2004/0254574 A1 | 12/2004 | Morrison et al. |
| 2004/0260283 A1 | 12/2004 | Wu et al. |
| 2004/0267264 A1 | 12/2004 | Konieczynski et al. |
| 2005/0010219 A1 | 1/2005 | Dalton |
| 2005/0021036 A1 | 1/2005 | Whitemore et al. |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0090821 A1 | 4/2005 | Berrevoets et al. |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131421 A1 | 6/2005 | Anderson et al. |
| 2005/0131422 A1 | 6/2005 | Anderson |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149053 A1 | 7/2005 | Varieur |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177154 A1 | 8/2005 | Moumene et al. |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192572 A1 | 9/2005 | Abdelgany et al. |
| 2005/0192573 A1 | 9/2005 | Abdelgany et al. |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Harms et al. |
| 2005/0203518 A1 | 9/2005 | Biederman et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228379 A1 | 10/2005 | Jackson |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |

(56) References Cited

U.S. PATENT DOCUMENTS

| | | |
|---|---|---|
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2006/0036242 A1 | 2/2006 | Nilsson et al. |
| 2006/0149232 A1 | 7/2006 | Sasing |
| 2006/0149235 A1 | 7/2006 | Jackson |
| 2006/0149238 A1 | 7/2006 | Sherman et al. |
| 2006/0173454 A1 | 8/2006 | Spitler et al. |
| 2006/0200128 A1 | 9/2006 | Mueller |
| 2006/0200131 A1 | 9/2006 | Chan et al. |
| 2006/0241603 A1 | 10/2006 | Jackson |
| 2006/0247635 A1 | 11/2006 | Gordon et al. |
| 2006/0247779 A1 | 11/2006 | Gordon |
| 2007/0129729 A1 | 6/2007 | Petit et al. |
| 2007/0219554 A1 | 9/2007 | Landry et al. |
| 2008/0051787 A1 | 2/2008 | Remington et al. |
| 2008/0086132 A1 | 4/2008 | Biedermann et al. |
| 2008/0091213 A1 | 4/2008 | Jackson |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0125813 A1 | 5/2008 | Erickson et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0140136 A1 | 6/2008 | Jackson |
| 2008/0147121 A1 | 6/2008 | Justis et al. |
| 2008/0147122 A1 | 6/2008 | Jackson |
| 2008/0147129 A1 | 6/2008 | Biedermann et al. |
| 2008/0147195 A1 | 6/2008 | Kwak et al. |
| 2008/0154279 A1 | 6/2008 | Schumacher et al. |
| 2008/0154308 A1 | 6/2008 | Sherman et al. |
| 2008/0154315 A1 | 6/2008 | Jackson |
| 2008/0161857 A1 | 7/2008 | Hestad et al. |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177321 A1 | 7/2008 | Drewry et al. |
| 2008/0177322 A1 | 7/2008 | Davis et al. |
| 2008/0177323 A1 | 7/2008 | Null et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0188898 A1 | 8/2008 | Jackson |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0228184 A1 | 9/2008 | Hestad |
| 2008/0228228 A1 | 9/2008 | Hestad et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234756 A1 | 9/2008 | Sutcliffe et al. |
| 2008/0234759 A1 | 9/2008 | Marino |
| 2008/0234761 A1 | 9/2008 | Jackson |
| 2008/0243052 A1 | 10/2008 | Pond et al. |
| 2008/0243185 A1 | 10/2008 | Felix et al. |
| 2008/0243193 A1 | 10/2008 | Ensign et al. |
| 2008/0249570 A1 | 10/2008 | Carson et al. |
| 2008/0262548 A1 | 10/2008 | Lange et al. |
| 2008/0262551 A1 | 10/2008 | Rice et al. |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0294203 A1 | 11/2008 | Kovach et al. |
| 2008/0300630 A1 | 12/2008 | Bonnema et al. |
| 2008/0300631 A1 | 12/2008 | Tornier |
| 2008/0300633 A1 | 12/2008 | Jackson |
| 2008/0306513 A1 | 12/2008 | Winslow et al. |
| 2008/0306525 A1 | 12/2008 | Winslow et al. |
| 2008/0306526 A1 | 12/2008 | Winslow et al. |
| 2008/0306533 A1 | 12/2008 | Winslow et al. |
| 2008/0306536 A1 | 12/2008 | Frigg et al. |
| 2008/0306540 A1 | 12/2008 | Mitchell et al. |
| 2008/0306543 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2008/0319482 A1 | 12/2008 | Jackson |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012562 A1 | 1/2009 | Hestad et al. |
| 2009/0012567 A1 | 1/2009 | Biedermann et al. |
| 2009/0018557 A1 | 1/2009 | Pisharodi |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0030464 A1 | 1/2009 | Hestad et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0062860 A1 | 3/2009 | Frasier et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082666 A1 | 3/2009 | Geist et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088769 A1 | 4/2009 | Poletti |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093846 A1 | 4/2009 | Hestad et al |
| 2009/0099606 A1 | 4/2009 | Hestad et al. |
| 2009/0099608 A1 | 4/2009 | Szczesny |
| 2009/0105769 A1 | 4/2009 | Rock et al. |

(56) References Cited

U.S. PATENT DOCUMENTS

| | | |
|---|---|---|
| 2009/0105770 A1 | 4/2009 | Berrevoets et al. |
| 2009/0105771 A1 | 4/2009 | Lei et al. |
| 2009/0105820 A1 | 4/2009 | Jackson |
| 2009/0112265 A1 | 4/2009 | Hudgins et al. |
| 2009/0112266 A1 | 4/2009 | Weng et al. |
| 2009/0112269 A1 | 4/2009 | Lieberman et al. |
| 2009/0118772 A1 | 5/2009 | Diederich et al. |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0149885 A1 | 6/2009 | Durward et al. |
| 2009/0149892 A1 | 6/2009 | Stad et al. |
| 2009/0157120 A1 | 6/2009 | Marino et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0177237 A1 | 7/2009 | Zucherman et al. |
| 2009/0182380 A1 | 7/2009 | Abdelgany |
| 2009/0182430 A1 | 7/2009 | Tyber et al. |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216278 A1 | 8/2009 | Song |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248083 A1 | 10/2009 | Patterson et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275985 A1 | 11/2009 | Jackson |
| 2009/0275986 A1 | 11/2009 | Prevost et al. |
| 2009/0281542 A1 | 11/2009 | Justis |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0281574 A1 | 11/2009 | Jackson |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2010/0004692 A1 | 1/2010 | Biedermann et al. |
| 2010/0004694 A1 | 1/2010 | Little |
| 2010/0004695 A1 | 1/2010 | Stad et al. |
| 2010/0010540 A1 | 1/2010 | Park |
| 2010/0010542 A1 | 1/2010 | Jackson |
| 2010/0010543 A1 | 1/2010 | Jackson |
| 2010/0023061 A1 | 1/2010 | Randol et al. |
| 2010/0030224 A1 | 2/2010 | Winslow et al. |
| 2010/0030272 A1 | 2/2010 | Winslow et al. |
| 2010/0030283 A1 | 2/2010 | King et al. |
| 2010/0036417 A1 | 2/2010 | James et al. |
| 2010/0036422 A1 | 2/2010 | Flynn et al. |
| 2010/0036423 A1 | 2/2010 | Hayes et al. |
| 2010/0036425 A1 | 2/2010 | Barrus et al. |
| 2010/0036432 A1 | 2/2010 | Ely |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0057125 A1 | 3/2010 | Viker |
| 2010/0057126 A1 | 3/2010 | Hestad |
| 2010/0057131 A1 | 3/2010 | Ely |
| 2010/0063544 A1 | 3/2010 | Butler |
| 2010/0063545 A1 | 3/2010 | Richelsoph |
| 2010/0063546 A1 | 3/2010 | Miller et al. |
| 2010/0063547 A1 | 3/2010 | Morin et al. |
| 2010/0063550 A1 | 3/2010 | Felix et al. |
| 2010/0063552 A1 | 3/2010 | Chin et al. |
| 2010/0069919 A1 | 3/2010 | Carls et al. |
| 2010/0069969 A1 | 3/2010 | Ampuero et al. |
| 2010/0082066 A1 | 4/2010 | Biyani |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0094343 A1 | 4/2010 | Pham et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0106192 A1 | 4/2010 | Barry |
| 2010/0114165 A1 | 5/2010 | Ely |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121386 A1 | 5/2010 | Peultier et al. |
| 2010/0125302 A1 | 5/2010 | Hammill, Sr. et al. |
| 2010/0137908 A1 | 6/2010 | Zhang |
| 2010/0137912 A1 | 6/2010 | Alcock et al. |
| 2010/0137918 A1 | 6/2010 | Wilcox et al. |
| 2010/0137920 A1 | 6/2010 | Hammill, Sr. et al. |
| 2010/0152776 A1 | 6/2010 | Keyer et al. |
| 2010/0152785 A1 | 6/2010 | Forton et al. |
| 2010/0160965 A1 | 6/2010 | Viker |
| 2010/0160967 A1 | 6/2010 | Capozzoli |
| 2010/0160968 A1 | 6/2010 | Joshi et al. |
| 2010/0160974 A1 | 6/2010 | Viker |
| 2010/0160976 A1 | 6/2010 | Biedermann et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0191293 A1 | 7/2010 | Jackson |
| 2010/0204735 A1 | 8/2010 | Gephart et al. |
| 2010/0211104 A1 | 8/2010 | Moumene et al. |
| 2010/0211105 A1 | 8/2010 | Moumene et al. |
| 2010/0211114 A1 | 8/2010 | Jackson |
| 2010/0222822 A1 | 9/2010 | Farris et al. |

(56) References Cited

U.S. PATENT DOCUMENTS

| | | |
|---|---|---|
| 2010/0222828 A1 | 9/2010 | Stad et al. |
| 2010/0228292 A1 | 9/2010 | Arnold et al. |
| 2010/0234902 A1 | 9/2010 | Biedermann et al. |
| 2010/0249843 A1 | 9/2010 | Wegrzyn, III |
| 2010/0249846 A1 | 9/2010 | Simonson |
| 2010/0249856 A1 | 9/2010 | Iott et al. |
| 2010/0262185 A1 | 10/2010 | Gelfand et al. |
| 2010/0262187 A1 | 10/2010 | Marik et al. |
| 2010/0262190 A1 | 10/2010 | Ballard et al. |
| 2010/0262191 A1 | 10/2010 | Marik et al. |
| 2010/0262192 A1 | 10/2010 | Foley |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0298891 A1 | 11/2010 | Jackson |
| 2010/0305621 A1 | 12/2010 | Wang et al. |
| 2010/0312288 A1 | 12/2010 | Hammill, Sr. et al. |
| 2010/0331885 A1 | 12/2010 | Remington et al. |
| 2011/0004256 A1 | 1/2011 | Biedermann et al. |
| 2011/0009906 A1 | 1/2011 | Hestad et al. |
| 2011/0009911 A1 | 1/2011 | Hammill et al. |
| 2011/0029022 A1 | 2/2011 | Zehnder et al. |
| 2011/0040338 A1 | 2/2011 | Jackson |
| 2011/0046683 A1 | 2/2011 | Biedermann et al. |
| 2011/0093015 A1 | 4/2011 | Ramsay et al. |
| 2011/0093021 A1 | 4/2011 | Fanger et al. |
| 2011/0106174 A1 | 5/2011 | Rezach |
| 2011/0106175 A1 | 5/2011 | Rezach |
| 2011/0130792 A1 | 6/2011 | Nydegger et al. |
| 2011/0152939 A1 | 6/2011 | Aldridge |
| 2011/0152949 A1 | 6/2011 | Biedermann et al. |
| 2011/0160778 A1 | 6/2011 | Elsbury |
| 2011/0166610 A1 | 7/2011 | Altarac et al. |
| 2011/0178558 A1 | 7/2011 | Barry |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0190822 A1 | 8/2011 | Spitler et al. |
| 2011/0196430 A1 | 8/2011 | Walsh |
| 2011/0202094 A1 | 8/2011 | Pereira et al. |
| 2011/0202095 A1 | 8/2011 | Semler et al. |
| 2011/0230915 A1 | 9/2011 | Anderson et al. |
| 2011/0238119 A1 | 9/2011 | Moumene et al. |
| 2011/0251644 A1 | 10/2011 | Hestad et al. |
| 2011/0257685 A1 | 10/2011 | Hay et al. |
| 2011/0257687 A1 | 10/2011 | Trieu et al. |
| 2011/0257689 A1 | 10/2011 | Fiechter et al. |
| 2011/0257690 A1 | 10/2011 | Rezach |
| 2011/0263945 A1 | 10/2011 | Peterson et al. |
| 2011/0313460 A1 | 12/2011 | Mclean et al. |
| 2011/0313463 A1 | 12/2011 | McLean |
| 2011/0313471 A1 | 12/2011 | McLean et al. |
| 2012/0029568 A1 | 2/2012 | Jackson |
| 2012/0046699 A1 | 2/2012 | Jones et al. |
| 2012/0053636 A1 | 3/2012 | Schmocker |
| 2012/0071928 A1 | 3/2012 | Jackson |
| 2012/0078307 A1 | 3/2012 | Nihalani |
| 2012/0197314 A1 | 8/2012 | Farris |
| 2012/0232598 A1 | 9/2012 | Hestad et al. |
| 2012/0310284 A1 | 12/2012 | Gerchow |
| 2013/0013003 A1* | 1/2013 | Carbone ............. A61B 17/863 606/305 |
| 2013/0103097 A1 | 4/2013 | May et al. |
| 2013/0150852 A1 | 6/2013 | Shluzas et al. |

FOREIGN PATENT DOCUMENTS

| | | |
|---|---|---|
| DE | 3630863 | 3/1988 |
| DE | G9202745.8 | 4/1992 |
| DE | 4425392 | 11/1995 |
| DE | 29806563 | 6/1998 |
| DE | 29810798 | 12/1999 |
| DE | 19951145 | 5/2001 |
| DE | 102007055745 | 7/2008 |
| EP | 0195455 | 9/1986 |
| EP | 0172130 | 2/1987 |
| EP | 0276153 | 7/1988 |
| EP | 0667127 | 8/1995 |
| EP | 0669109 | 8/1995 |
| EP | 0677277 | 10/1995 |
| EP | 1277444 | 1/2003 |
| EP | 1449486 A1 * | 8/2004 ......... A61B 17/7032 |
| EP | 2082709 | 7/2009 |
| EP | 2468198 | 12/2010 |
| ES | 2384773 | 7/2012 |
| FR | 2467312 | 4/1981 |
| FR | 2715825 | 8/1995 |
| FR | 2717370 | 9/1995 |
| FR | 2718946 | 10/1995 |
| FR | 2799949 | 4/2001 |
| FR | 2814936 | 4/2002 |
| FR | 2815535 | 4/2002 |
| FR | 2856578 | 6/2003 |
| FR | 2925288 | 6/2009 |
| GB | 203508 | 9/1923 |
| GB | 2082709 | 3/1982 |
| GB | 2140523 | 11/1984 |
| GB | 2365345 | 2/2002 |
| GB | 2382304 | 5/2003 |
| JP | S4867159 | 9/1973 |
| JP | S50106061 | 8/1975 |
| JP | H10277070 | 10/1998 |
| JP | 2000325358 | 3/2000 |
| JP | 2002052030 | 2/2002 |
| JP | 2002221218 | 8/2002 |
| SU | 371359 | 2/1973 |
| WO | 8909030 | 10/1989 |
| WO | 8912431 | 12/1989 |
| WO | 9116018 | 10/1991 |
| WO | 9116020 | 10/1991 |
| WO | 9203100 | 3/1992 |
| WO | 9321848 | 11/1993 |
| WO | 9325161 | 12/1993 |
| WO | 9410927 | 5/1994 |
| WO | 9410944 | 5/1994 |
| WO | 9426191 | 11/1994 |
| WO | 9428824 | 12/1994 |
| WO | 9501132 | 1/1995 |
| WO | 9513755 | 5/1995 |
| WO | 9528889 | 11/1995 |
| WO | 9531947 | 11/1995 |
| WO | 9535067 | 12/1995 |
| WO | 9606576 | 3/1996 |
| WO | 9621396 | 7/1996 |
| WO | 9625104 | 8/1996 |
| WO | 9628105 | 9/1996 |
| WO | 9628118 | 9/1996 |
| WO | 9641582 | 12/1996 |
| WO | 9714366 | 4/1997 |
| WO | 9714368 | 4/1997 |
| WO | 9727812 | 8/1997 |
| WO | 9730649 | 8/1997 |
| WO | 9737604 | 10/1997 |
| WO | 9737605 | 10/1997 |
| WO | 9812977 | 4/1998 |
| WO | 9815233 | 4/1998 |
| WO | 9825534 | 6/1998 |
| WO | 9832386 | 7/1998 |
| WO | 9834554 | 8/1998 |
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 0015125 | 3/2000 |
| WO | 0022997 | 4/2000 |
| WO | 0027297 | 5/2000 |
| WO | 0072769 | 7/2000 |
| WO | 0065268 | 11/2000 |
| WO | 0066045 | 11/2000 |

(56) References Cited

FOREIGN PATENT DOCUMENTS

| | | |
|---|---|---|
| WO | 0106940 | 2/2001 |
| WO | 0108574 | 2/2001 |
| WO | 0110317 | 2/2001 |
| WO | 0115612 | 3/2001 |
| WO | 0122893 | 4/2001 |
| WO | 0128435 | 4/2001 |
| WO | 0128436 | 4/2001 |
| WO | 0145576 | 6/2001 |
| WO | 0149191 | 7/2001 |
| WO | 0158370 | 8/2001 |
| WO | 0167972 | 9/2001 |
| WO | 0167974 | 9/2001 |
| WO | 0222030 | 3/2002 |
| WO | 0234150 | 5/2002 |
| WO | 02054966 | 7/2002 |
| WO | 02102259 | 12/2002 |
| WO | 03007828 | 1/2003 |
| WO | 03026523 | 4/2003 |
| WO | 03037199 | 5/2003 |
| WO | 03047442 | 6/2003 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007118045 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124222 | 11/2007 |
| WO | 2007124249 | 11/2007 |
| WO | 2007127595 | 11/2007 |
| WO | 2007127604 | 11/2007 |
| WO | 2007130835 | 11/2007 |
| WO | 2007130840 | 11/2007 |
| WO | 2007130941 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008008511 | 1/2008 |
| WO | 2008013892 | 1/2008 |
| WO | 2008027860 | 3/2008 |
| WO | 2008033742 | 3/2008 |
| WO | 2008036975 | 3/2008 |
| WO | 2008037256 | 4/2008 |
| WO | 2008039777 | 4/2008 |
| WO | 2008042948 | 4/2008 |
| WO | 2008048923 | 4/2008 |
| WO | 2008048953 | 4/2008 |
| WO | 2008051737 | 4/2008 |
| WO | 2008069420 | 6/2008 |
| WO | 2008070716 | 6/2008 |
| WO | 2008134703 | 6/2008 |
| WO | 2008078163 | 7/2008 |
| WO | 2008082737 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009015100 | 1/2009 |
| WO | 2009018086 | 2/2009 |
| WO | 2009029928 | 3/2009 |
| WO | 2009055028 | 4/2009 |
| WO | 2009055400 | 4/2009 |
| WO | 2009055407 | 4/2009 |
| WO | 2009152302 | 12/2009 |
| WO | 2009155360 | 12/2009 |
| WO | 2010017631 | 2/2010 |
| WO | 2010018316 | 2/2010 |
| WO | 2010018317 | 2/2010 |
| WO | 2010019857 | 2/2010 |
| WO | 2010030916 | 3/2010 |
| WO | 2010045383 | 4/2010 |
| WO | 2010065648 | 6/2010 |
| WO | 2010078901 | 7/2010 |
| WO | 2010111500 | 9/2010 |
| WO | 2010120989 | 10/2010 |
| WO | 2010147639 | 12/2010 |
| WO | 2011043805 | 4/2011 |
| WO | 2011068818 | 6/2011 |
| WO | 2012033532 | 3/2012 |
| WO | 2012075827 | 6/2012 |
| WO | 2012088890 | 7/2012 |

OTHER PUBLICATIONS

CD Horizon M8 Multi Axial Screw Spinal System Brochure, Medtronic Sofamor Danek, no publish date.
Claris Instrumentation Brochure, G Med, pub. 1997.
Contour Spinal System Brochure, Ortho Development, no publish date.
EBI Omega 21 Brochure, EBI Spine Systems, pub. 1999.
SDRS Surgical Dynamics Rod System Brochure, Surgical Dynamics, pub. 1998-99.
Silhouette Spinal Fixation System Brochure, Sulzer Medica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.
Brochure of DePuySpine on Surgical Technique, Published 2004, pp. 1-36.

* cited by examiner

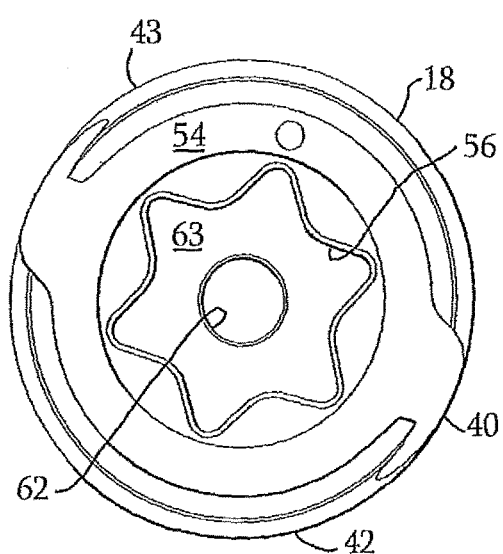
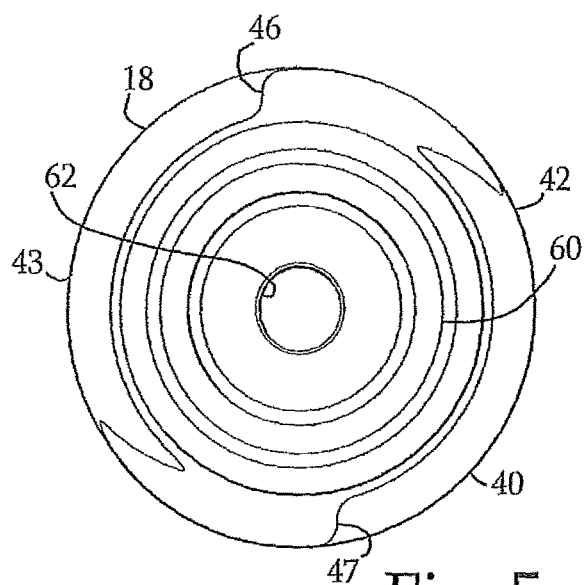
Fig. 4      Fig. 5
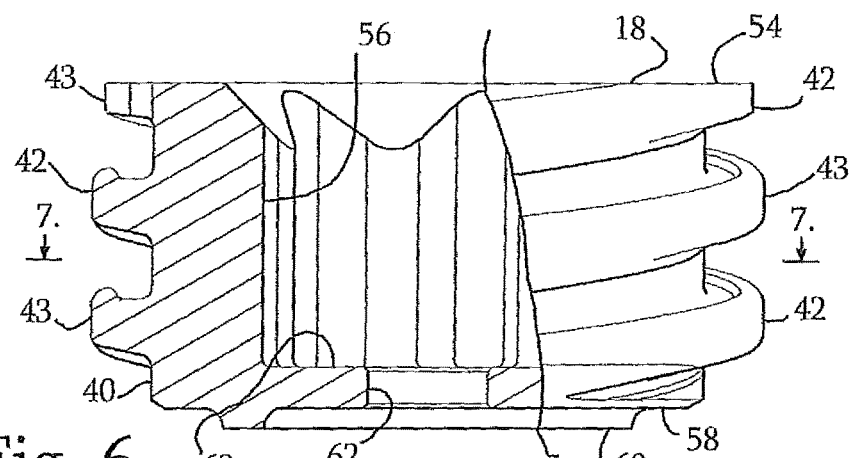
Fig. 6
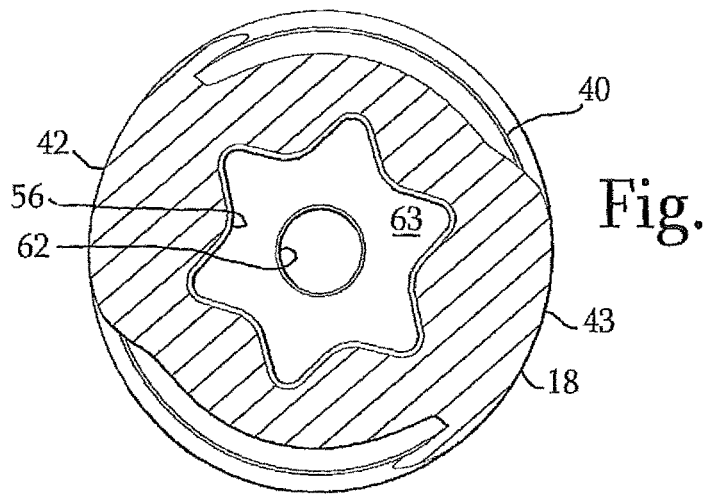
Fig. 7

Fig. 15.
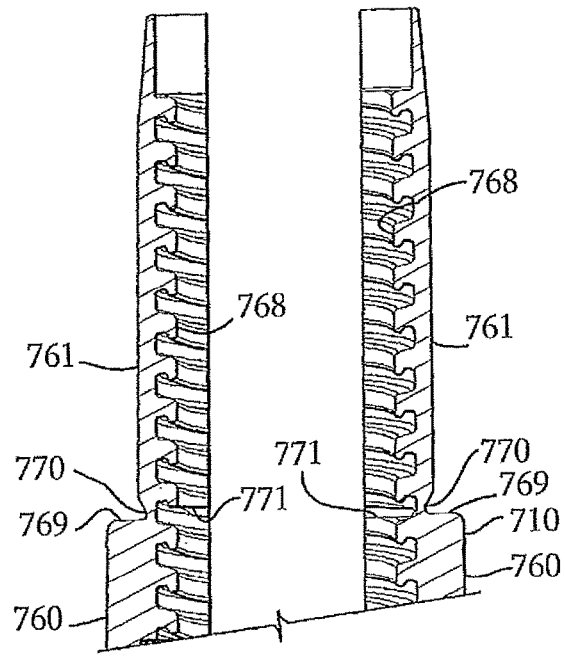
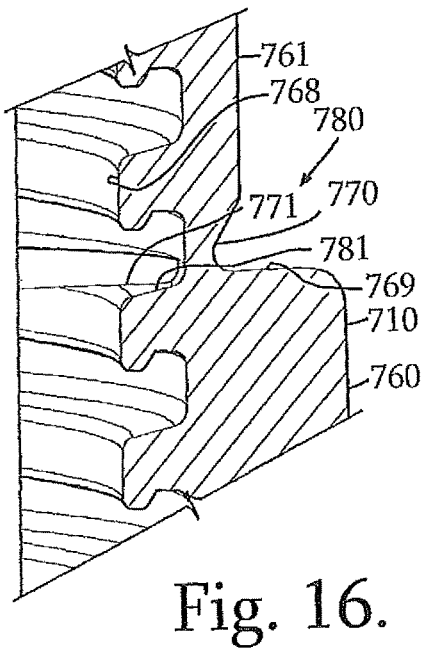
Fig. 16.
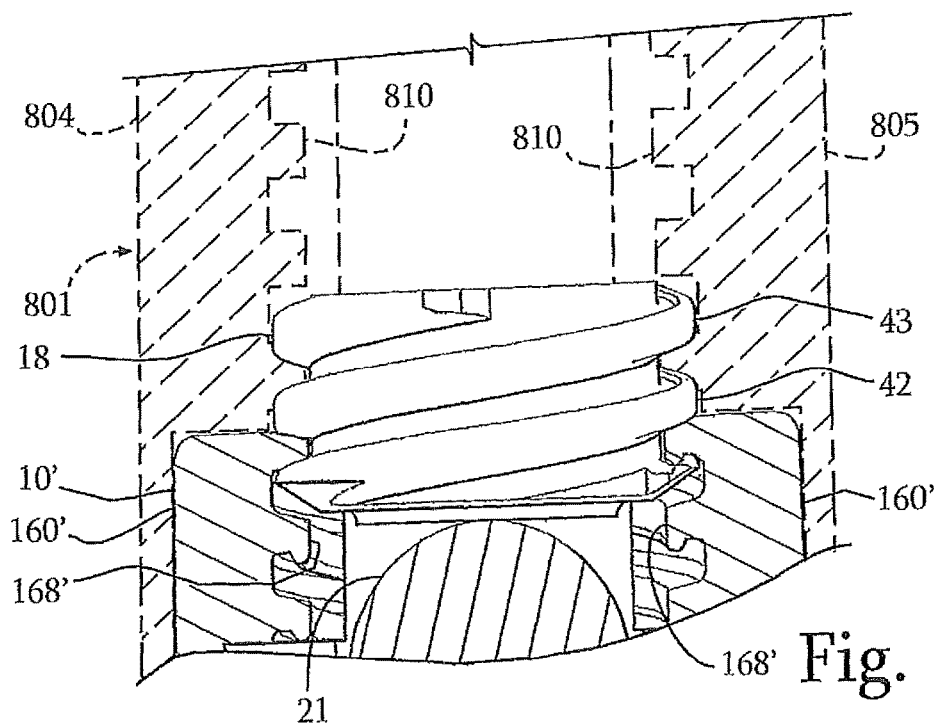
Fig. 17.

MULTI-START CLOSURES FOR OPEN IMPLANTS

CROSS-REFERENCE TO RELATED APPLICATIONS

This application is a continuation of U.S. patent application Ser. No. 13/694,849, filed Jan. 10, 2013, now U.S. Pat. No. 8911479, which claims the benefit of U.S. Provisional Patent Application Ser. No. 61/631,746 filed Jan. 10, 2012 that are each incorporated by reference herein. U.S. patent application Ser. No. 13/694,849 also claims the benefit of U.S. Provisional Patent Application Ser. No. 61/634,361 filed Feb. 28, 2012, that is incorporated by reference herein.

BACKGROUND OF THE INVENTION

The present invention is directed to structure for joining together parts of a medical implant, in particular to closure mechanisms for use with open bone anchors in spinal surgery, and in some embodiments thereof, for use with spinal bone anchors such as polyaxial screws.

Bone anchors, such as bone screws and hooks are utilized in many types of spinal surgery in order to secure various implants to vertebrae along the spinal column for the purpose of stabilizing and/or adjusting spinal alignment. For example, the most common mechanism for providing vertebral support is to implant bone screws into certain bones which then in turn support a rod or are supported by the rod. Although both closed-ended and open-ended bone anchors are known, open-ended anchors are particularly well suited for connections to longitudinal connecting members such as hard, soft or deformable rods, dynamic or elastic connectors and connector arms, because such rods or other connector members do not need to be passed through a closed bore, but rather can be laid or urged into an open channel within a receiver or head of such a bone anchor. Generally, the anchors must be inserted into the bone as an integral unit or a preassembled unit, in the form of a shank or hook and connected pivotal receiver. In some instances, a portion of such a preassembled unit, such as a shank of a polyaxial bone screw assembly, may be independently implanted into bone, followed by push- or pop-on assembly of a receiver portion of the unit.

Typical open-ended bone screws include a threaded shank with a head or receiver having a pair of parallel projecting branches or arms which form a yoke with a U-shaped slot or channel to receive a rod or other longitudinal connecting member. Hooks and other types of connectors, as are used in spinal fixation techniques, may also include similar open ends for receiving rods or portions of other fixation and stabilization structure. The open-ended head or rod receiver portion of such implants typically includes a pair of spaced arms forming a channel closed by a closure member after the rod or other longitudinal connecting member is placed in the channel. Known closures include slide-on types, twist-on varieties that are rotated ninety degrees to a locked in position, and a variety of single start helically wound guide and advancement structures including, for example, thread forms having v-thread, reverse-angle buttress or square thread forms, to name a few, as well as other non-threadlike helically wound forms. Sometimes threaded plugs are utilized with outer threaded nuts to prevent splaying of the receiver arms.

As indicated above, the force required to press a closure structure down onto a rod or other connector located between arms of an open implant is considerable. Even though a head or receiver portion of an open polyaxial bone anchor may be pivoted in a direction to make it easier for the arms of the open implant to receive a rod or other connector, spinal misalignments, irregularities and the placement of other surgical tools make it difficult to place the rod or other connector between the arms of the implant while a closure structure is mated with the open implant as well as used to push the rod or other connector downwardly into the implant. For example, when the closure is a cylindrical plug having a single start helically wound guide and advancement structure, such structure must be aligned with mating structure on one of the implant arms and then rotated until a portion of the structure is captured by mating guide and advancement structure on both arms of the implant, all the while the closure is being pressed down on the rod while other forces are pushing and pulling the rod back out of the implant. Integral or mono-axial open implants that cannot be pivoted to receive the rod are even more difficult to manipulate during the initial placement of the rod and initial mating rotation of a closure plug between the spaced, open arms of the implant. Therefore, extraordinary forces are placed on the implant and closure plug while the surgeon either pushes down on the rod or pulls up on the bone to get the rod in position between the implant arms and to initially push down upon the rod with the closure plug.

SUMMARY OF THE INVENTION

A closure structure, top or plug of the invention for insertion between spaced arms of an open medical implant includes one or more helically wound guide and advancement features, each feature having a start surface or structure located at or near a bottom surface of the closure plug, each start structure simultaneously engaging and being captured by each of the spaced arms of the open implant upon initial rotation of the closure structure with respect to the open implant arms. According to an aspect of the invention, a double-start closure is disclosed having two helically wound forms thereon, each form having a start structure for simultaneously engaging a mating helical form on a respective open implant arm. Each time the illustrated duel- or double-start closure plug is rotated one turn (three hundred sixty degrees) between the implant arms, the closure plug advances axially into the implant and toward the rod by a width of two helical forms. The helically wound forms of the multi-start closure spiral around a cylindrical plug body thereof to an extent that the closure rotates over ninety degrees to fully or substantially receive the entire closure plug between the arms of the open implant. The illustrated closure is sized for at least one complete rotation (three hundred sixty degrees) of the plug with respect to the open implant to substantially receive the plug between the implant arms. Multi-start closures of the invention may have two or more coarse or fine helical forms, resulting in fewer or greater forms per axial distance spiraling about the closure plug body and thus resulting in plugs that rotate less (when more coarse) or more (when thin or fine) than one complete rotation to be fully received between the implant arms, typically, at least a ninety-one degree rotation is preferred.

An illustrated multi-start closure and mating open implant is in the form of non-threaded, interlocking flange forms. Also disclosed are multi-start closure structures provided with helically wound forms of other geometry, including, but not limited to helically wound threads such as reverse angle, buttress, square and v-threads. The multi-start closure may be cannulated for minimally invasive surgical applications.

Another illustrated multi-start closure embodiment of the invention is shown with a bone screw assembly having an open receiver with a pair of opposed arms, each arm having guide and advancement structure for simultaneous mating engagement with a start of the helically wound multi-start closure. A further embodiment according to the invention includes an open bone anchor receiver having integral upwardly extending break-off tabs that also have the guide and advancement structure for mating with the multi-start closure. A further embodiment includes an attachable/detachable guide tool cooperating with such a multi-start open receiver, the tool having inner guide and advancement structures located near a bottom thereof for rotatably and matingly receiving the multi-start closure and being synchronized with the receiver guide and advancement structure for rotating and driving the multi-start closure downward from the guide tool to the receiver.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is a reduced top plan view of the closure of FIG. 1.

FIG. 5 is a reduced bottom plan view of the closure of FIG. 1.

FIG. 6 is an enlarged front elevational view of the closure of FIG. 1 with portions broken away to show the detail thereof.

FIG. 7 is a reduced cross-sectional view taken along the line 7-7 of FIG. 6.

FIG. 15 is a partial front elevational view of an embodiment of a multi-start open bone anchor receiver of an embodiment of the invention with portions broken away to show the detail thereof, the receiver including break-off tabs.

FIG. 16 is an enlarged and partial front elevational view of the receiver of FIG. 15 with portions broken away to show the detail thereof.

FIG. 17 is a partial front elevational view of an embodiment of a bone anchor receiver having a guide and advancement structure that matingly cooperates with the multi-start closure of FIG. 1, also shown in front elevation, the receiver having portions broken away to show the detail thereof, and further shown with a guide tool, shown in phantom, the guide tool having a multi-start guide and advancement structure receiving inner surface synchronized with the bone anchor receiver guide and advancement structure.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Furthermore, the terms lead, pitch and start, as such terms are used to describe helically wound guide and advancement structures, are to be understood as follows: Lead is a distance along the axis of a closure plug that is covered by one complete rotation (360 degrees) of the closure plug with respect to a mating open implant. Pitch is the distance from a crest (or outer point or location) of one guide and advancement structure form to the next. For example in a single-start thread-form, such as a single start, helically wound v-thread closure plug, lead and pitch are the same. Single start means that there is only one ridge or helically wound form wrapped around a cylindrical core, or in the case of the present invention, wrapped around a cylindrical closure plug body and thus there is only one start structure or surface at a base or forward end of the closure body that initially engages a mating structure on the open implant. Each time a single start closure rotates one turn (360 degrees), the closure has advanced axially by a width of one ridge or one helical form. Double-start means that there are two ridges or forms wrapped around a core body and thus there are two starting surfaces or structures on the closure plug. Therefore, each time a double-start body rotates one turn (360 degrees), such a body has advanced axially by a width of two ridges or forms. Multi-start means that there are at least two and may be up to three or more of such ridges or forms wrapped around a core body.

Figure 8:
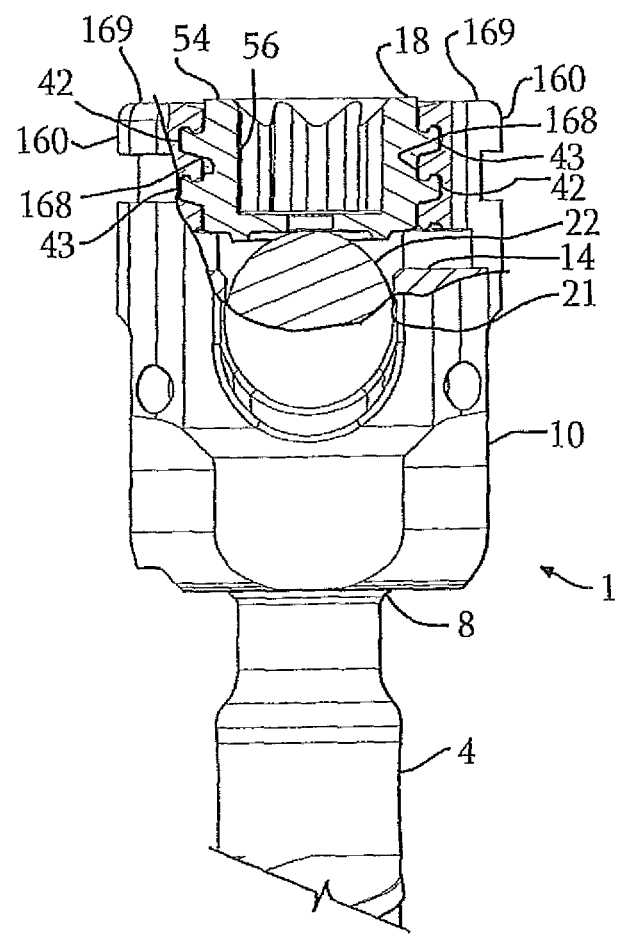
FIG. 8 a partial front elevational view of an open bone screw assembly, with portions broken away to show the detail thereof, including a receiver, a shank, a compression insert and also shown in engagement with the closure top of FIG. 1 (in reduced view) and a longitudinal connecting member in the form of a hard rod.

With reference to FIGS. 1-8, and in particular to FIG. 8, the reference number 1 generally represents an open implant in the form of a polyaxial bone screw apparatus or assembly that cooperates with an illustrated closure structure 18 embodiment of the invention. The bone screw assembly 1 is described in detail in U.S. Provisional Patent Application No. 61/631,746 filed Jan. 10, 2012 and incorporated by reference herein (hereafter the '746 application) and therefore will not be described in great detail herein. The description set forth in the '746 application includes a more detailed explanation of all the components referenced in FIG. 8. It is noted that multi-start closure embodiments of the invention, such as the closure 18 may be used with a variety of open implants including, but not limited to a wide variety of polyaxial screws, mono-axial or fixed screws, hooks and other types of open implants requiring a plug or closure mechanism to fix a rod or other implant member to a vertebra or other bone. Thus, the assembly 1 is only one example of how multi-start closures of the invention may be used.

Briefly, the illustrated assembly 1 includes a shank 4 with an upwardly extending upper portion or capture structure 8; an open receiver 10; a retaining structure or retainer (not shown) that pivots with the shank 4, a compression or pressure insert 14 and the multi-start closure structure or plug 18 in the form of a cylindrical plug having a double-start helically wound flange-form. The closure structure 18 presses against and captures a longitudinal connecting member, for example, a rod 21 which in turn engages the compression insert 14 that presses against the shank upper portion 8 that is attached to the retaining structure that in turn presses against an inner surface of the receiver 10, so as to capture and fix the longitudinal connecting member 21 within the receiver 10 and thus fix the member 21 relative to a vertebra (not shown). The illustrated receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The illustrated rod 21 is hard, stiff, non-elastic and cylindrical, having an outer cylindrical surface 22. However, in other embodiments, the rod 21 may be elastic, deformable and/or of a different cross-sectional geometry. The rod 21 may be made from a variety of metals, metal alloys and deformable and less compressible plastics, including, but not limited to rods made of elastomeric, polyetheretherketone (PEEK) and other types of materials, such as polycarbonate urethanes (PCU) and polyethylenes. Furthermore, in lieu of a rod, longitudinal connecting members for use with the assembly 1 may take a variety of shapes, and/or may include a tensioned cord as described in greater detail in the '746 application that is incorporated by reference herein.

It is noted that the receiver 10 includes guide and advancement structures 168 that are shown as interlocking flange forms described in greater detail in applicant's U.S. Pat. No. 6,726,689, also incorporated by reference herein. Alternately, when the closure structure includes a different helical form, the receiver cooperating structures (e.g., 168) must also be of a cooperating, mating geometry, such as a square-shaped thread receiving form, a buttress thread receiving form, a reverse angle thread receiving form or other thread-like or non-thread-like helically wound discontinuous advancement structure receiving forms for operably guiding under rotation and advancing a multi-start closure structure downward between the receiver arms 160, as well as eventual torquing when the closure structure abuts against the rod 21 or other connecting member.

With particular reference to FIGS. 1-7, the illustrated multi-start closure structure 18 is a double start closure having a substantially cylindrical plug body 40 having an axis of rotation that is the same as that of the receiver 10 and including a helically wound guide and advancement structure in the form of a pair of helically wound forms 42 and 43, each illustrated as an interlocking flange form that operably joins with mating flange form guide and advancement structures 168 disposed on the arms of the receiver 10. The form 42 includes a start surface or structure 46 and the form 43 includes a start surface or structure 47. Each helically wound form 42 and 43 may take a variety of forms and geometries, including those described in Applicant's U.S. Pat. No. 6,726,689, which is incorporated by reference herein. It is noted (and also described in greater detail subsequently herein) that each of the closure structure guide and advancement structures or forms 42 and 43 could alternatively be in the form of a buttress thread, a square thread, a reverse angle thread, a v-thread or other thread like or non-thread like helically wound advancement structures, for operably guiding under rotation and advancing the closure structure downward between the arms of the receive 10 and preferably having such a nature as to resist splaying of the receiver arms when the closure structure 18 is advanced into the receiver channel. The specific flange forms 42 and 43 illustrated in FIGS. 1-7, as well as acceptable alternative locking forms, are described in detail in Applicant's U.S. Pat. No. 6,726,689, incorporated by reference herein, and thus shall not be discussed further herein. Such interlocking flange forms are preferred as the added strength provided thereby beneficially cooperate with and counter any reduction in strength caused by the any reduced profile of the receiver 10 that may more advantageously engage longitudinal connecting member components.

The illustrated closure structure 18 also includes a top surface 54 with an internal drive 56 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 56 is used for both rotatable engagement and, if needed, disengagement of the closure 18 from the receiver 10 at arms 160. A base or bottom surface 58 of the closure is planar and further includes a rim 60 for engagement and penetration into the surface 22 of the rod 21 in certain embodiments of the invention. The closure top 18 further includes a cannulation through bore 62 extending along a central axis thereof and through a drive base surface 63 and the bottom surface 58 thereof. Such a through bore provides a passage through the closure 18 interior for a length of wire (not shown) inserted therein to provide a guide for insertion of the closure top into the receiver arms 160.

Figure 1:
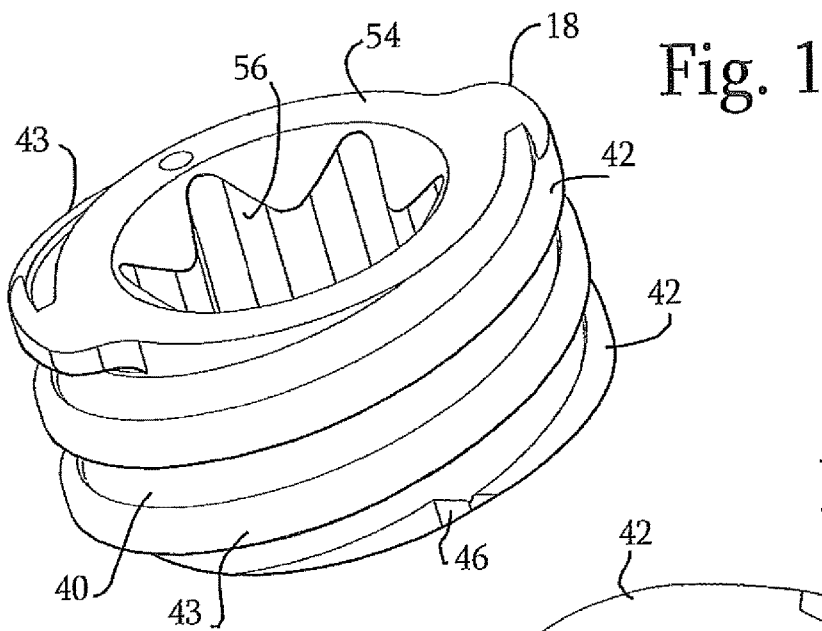
FIG. 1 is a perspective view of an embodiment of a multi-start closure according to the invention.
Figure 2:
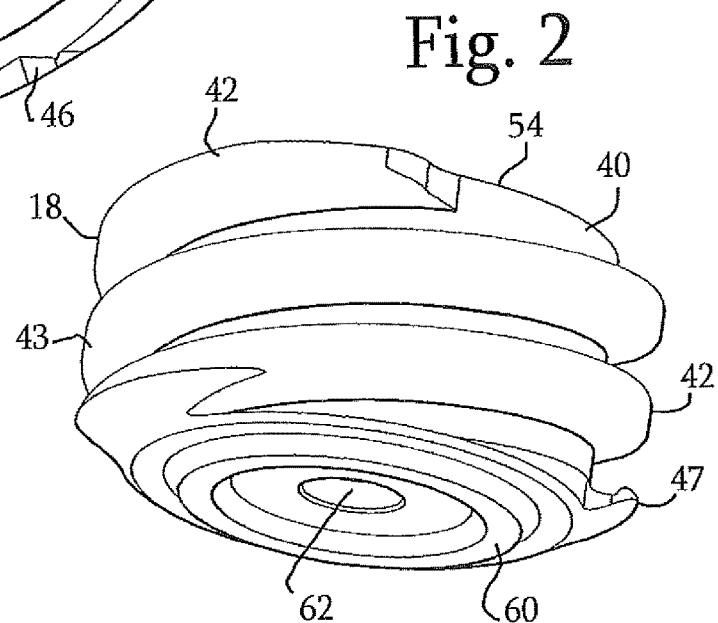
FIG. 2 is another perspective view of the multi-start closure of FIG. 1.
Figure 3:
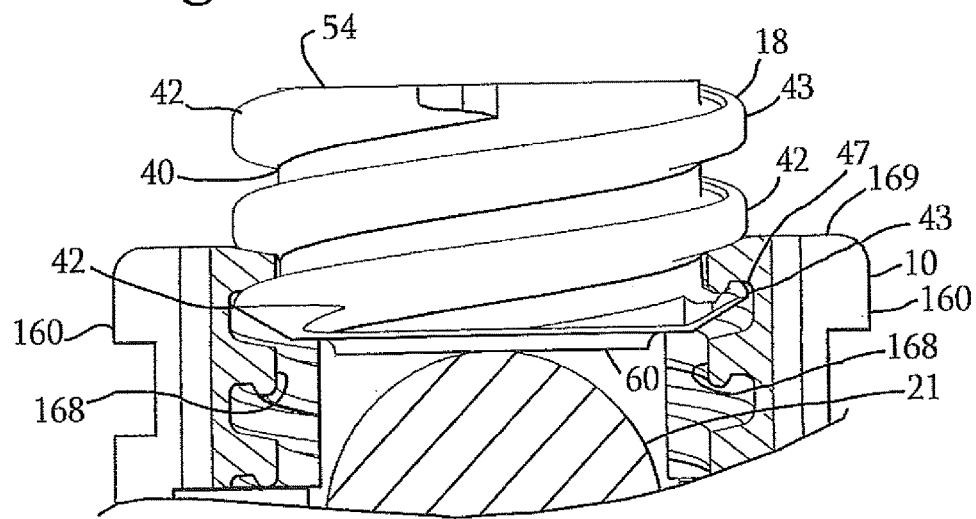
FIG. 3 is a front elevational view of the closure of FIG. 1 shown with a portion of a receiver of a polyaxial bone screw according to FIG. 8, the receiver shown in partial front elevation with portions broken away to show the detail thereof, and further showing a rod being pressed upon by the closure, the rod also in partial front elevation with portions broken away to show the detail thereof.

The closure structure 18 helically wound flange form start structures 46 and 47 of the respective forms 42 and 43 are located on opposite sides of the closure plug body 40 and are both located adjacent the bottom surface 58. As illustrated in FIG. 3, for example, when the closure structure 18 is rotated into the receiver 10 between receiver arms 160, each having a guide and advancement structure 168, the start 46 engages mating guide and advancement structure 168 on one arm 160 and the start 47 simultaneously engages guide and advancement structure 168 on the opposing arm 160, both forms 42 and 43 being simultaneously captured by the mating forms 168 on the opposed arms 160. As the structure 18 is rotated, the structure advances axially downwardly between the arms 160 and presses evenly down upon the captured rod 21. Each time the illustrated duel- or double-start closure plug 18 is rotated one complete turn or pass (three hundred sixty degrees) between the implant arms, the closure plug 18 advances axially into the implant and toward the rod by a width of two helical flange forms. The illustrated closure 18 is sized for at least one complete rotation (three hundred sixty degree) of the plug 18 with respect to the receiver 10 open arms 160 to substantially receive the plug between the implant arms. Multi-start closures of the invention may have two or more coarse or fine helical forms, resulting in fewer or greater forms per axial distance spiraling about the closure plug body and thus resulting in plugs that rotate less or more than one complete rotation to be fully received between the implant arms. Preferably, helically wound forms of the multi-start closure of the invention are sized so as to spiral around a cylindrical plug body thereof to an extent that the closure rotates at least ninety-one degrees to fully or substantially receive the closure plug between the arms of the bone screw receiver or other open implant. Particularly preferred guide and advancement structures are sized for at least one complete turn or pass (three-hundred sixty degree) of the closure between the receiver 10 arms and as many as two to three rotations to be fully received between implant arms.

In use, the receiver 10, the retainer 12 and the compression insert 14 are assembled with the shank 4 either before or after the shank is implanted into a vertebra, and the resulting assembly 1 is ultimately attached to the rod 21 or other longitudinal connecting member as described in the '746 application incorporated by reference herein. It is noted that the shank 4 and other bone screw assembly parts, the rod 21 (also having a central lumen in some embodiments) and the closure top 18 having the central bore 62 can be inserted in a percutaneous or minimally invasive surgical manner, utilizing guide wires. After the rod 21 or other longitudinal connecting member is positioned in an open or percutaneous manner in cooperation with the at least two bone screw assemblies 1 (or other open implants), the closure structure 18 is then inserted into and advanced between the arms 160 of each of the receiver 10. The closure structure 18 is rotated, using a tool engaged with the inner drive 56 until a selected pressure is reached at which point the rod 21 engages a U-shaped seating surface of the compression insert 14, further pressing the insert against the shank upper portion 8 and attached retainer into locked frictional engagement with the receiver 10. Prior to locking the insert 14 against the shank head 8, the shank 4 may be pivoted to a plurality of potentially desirable positions with respect to the receiver 10, followed by locking of the polyaxial mechanism by fully mating the multi-start closure top 18 with the receiver 10. Different angular or articulated positions of the shank 4 with respect to the receiver 10 are shown in the '746 application incorporated by reference herein.

With specific reference to FIGS. 3 and 8, as the multi-start closure structure 18 rotates and moves downwardly into the respective receiver 10, the rim 60 engages and penetrates the rod surface 22, the closure structure 18 pressing downwardly against and biasing the rod 21 into compressive engagement with the insert 14 that urges the shank upper portion 8 and attached retainer into locking engagement with the receiver, the retainer outer surface frictionally abutting an inner spherical seating surface of the receiver 10. For example, about 80 to about 120 inch pounds of torque on the closure top may be applied for fixing the bone screw shank 6 with respect to the receiver 10. Also, for example, when the shank 4 is disposed at an angle with respect to the receiver 10, a part of the shank upper portion 8 may also be in frictional engagement with a portion of the receiver spherical seating surface.

If removal of the rod 21 from any of the bone screw assemblies 1 is necessary, or if it is desired to release the rod 21 at a particular location, disassembly is accomplished by using the driving tool (not shown) that mates with the internal drive 56 on the closure structure 18 to rotate and remove such closure structure from the cooperating receiver 10. Disassembly is then accomplished in reverse order to the procedure described previously herein for assembly.

Figure 9:
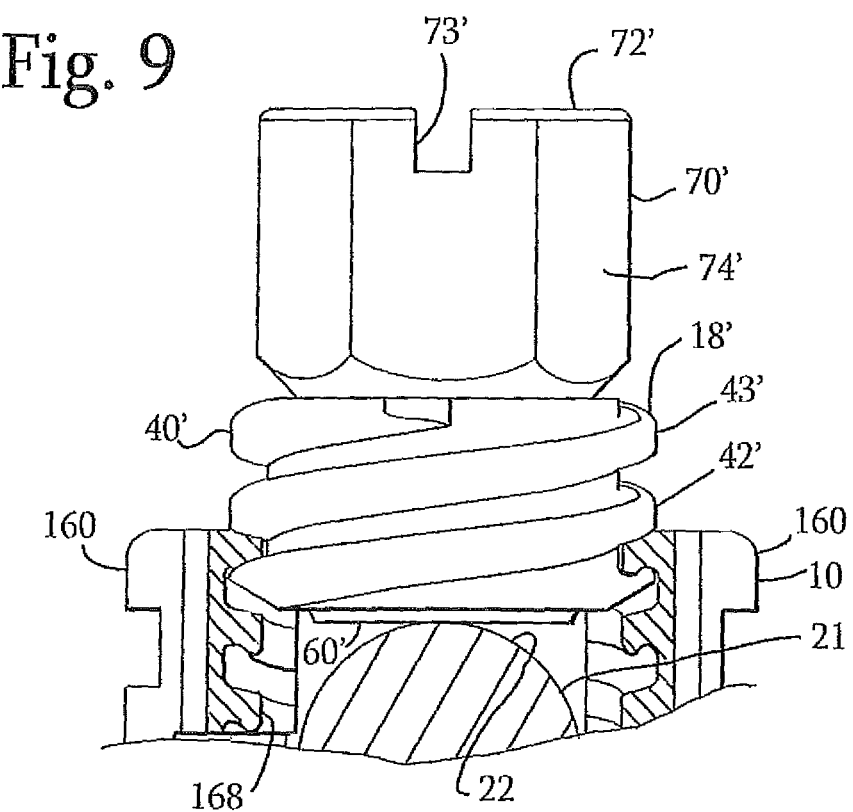
FIG. 9 is a front elevational view of an alternative closure of an embodiment of the invention, similar to the closure of FIG. 1, but including a break-off head, the alternative closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.
Figure 10:
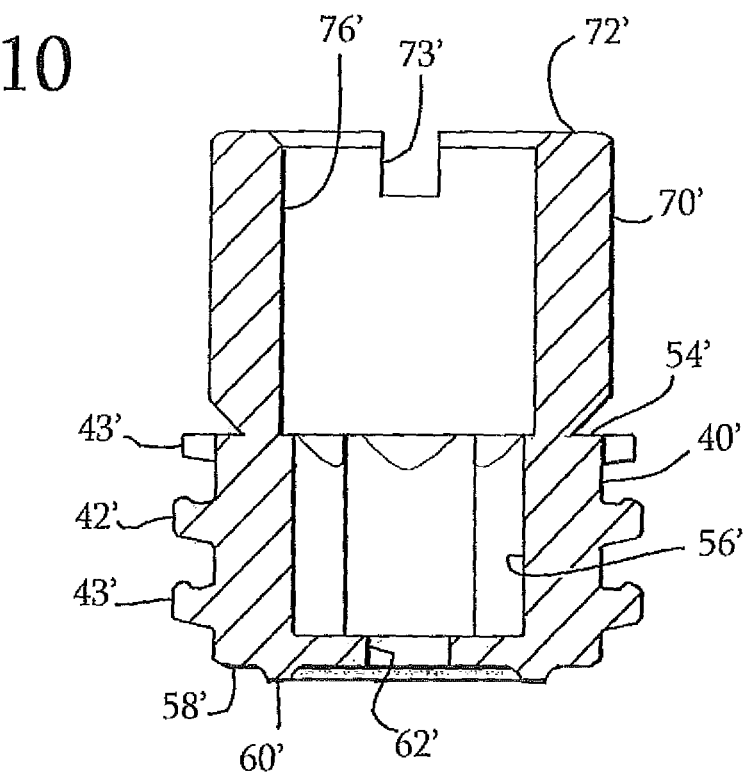
FIG. 10 is another front elevational view of the closure of FIG. 9 with portions broken away to show the detail thereof.

With reference to FIGS. 9 and 10, an alternative closure top 18' is shown that is almost identical to the closure top 18. However, the top 18' differs from the top 18 in that the top 18' includes a break-off head 70' that further includes a top surface 72' having tooling notches 73', an outer faceted driving surface 74', illustrated as having a hex-shaped profile, and an inner bore 76'. Otherwise, the closure top 18' includes a body 40', a first helical form 42', a second helical form 43', a body top surface 54', a body internal drive 56', a base 58', a rim 60', a cannulation bore 62' and a drive base surface 63' that is the same or substantially similar to the respective body 40, first helical form 42, second helical form 43, body top surface 54, internal drive 56, base 58, rim 60, cannulation bore 62 and drive base surface 63 previously described herein with respect to the closure top 18. The break-off head 70' is integral with the body 40' at the body top surface 54'. The inner bore 76' communicates with the inner drive 56' and the cannulation bore 62'. The break-off head 70' is designed to allow such head 70' to break from the body 40' at or near the top surface 54' at a preselected torque, for example, 70 to 140 inch pounds, when a hex-shaped tool (not shown) engages the outer surfaces 74' and drives the closure structure 18' into the receiver 10 as shown in FIG. 9. The inner drive 56' is used for disassembly or loosening of the closure 18' from the receiver 10, and re-tightening, if needed.

Figure 11:
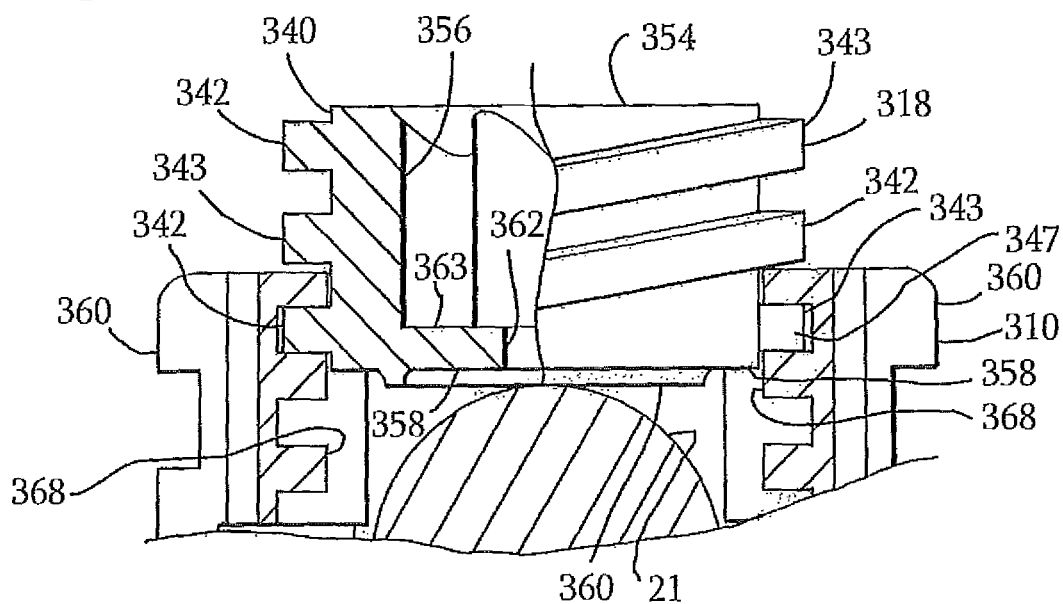
FIG. 11 is a front elevational view of an alternative square-thread closure of an embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 11, another alternative multi-start closure top 318 is shown that is almost identical to the closure top 18 with the exception that the two flange forms 42 and 43 with respective starts 46 and 47 have been replaced with square threads 342 and 343 with respective starts 346 (not shown) and 347. Otherwise, the dual or double start closure top 318 includes a body 340, a body top surface 354, a body internal drive 356, a base 358, a rim 360', a cannulation bore 362 and a drive base surface 363 that is the same or substantially similar to the respective body 40, body top surface 54, internal drive 56, base 58, rim 60, cannulation bore 62 and drive base surface 63 previously described herein with respect to the closure top 18. In FIG. 11, the closure top 318 is shown partially wound into a polyaxial bone screw receiver 310 having opposed arms 360 with inner surfaces equipped with guide and advancement structures 368 that are sized and shaped to simultaneously closely receive and mate with the square threads 342 and 343 of the double closure structure 318. Otherwise, the receiver 310 is identical or substantially similar to the receiver 10 described in detail in the '746 application incorporated by reference herein.

Figure 12:
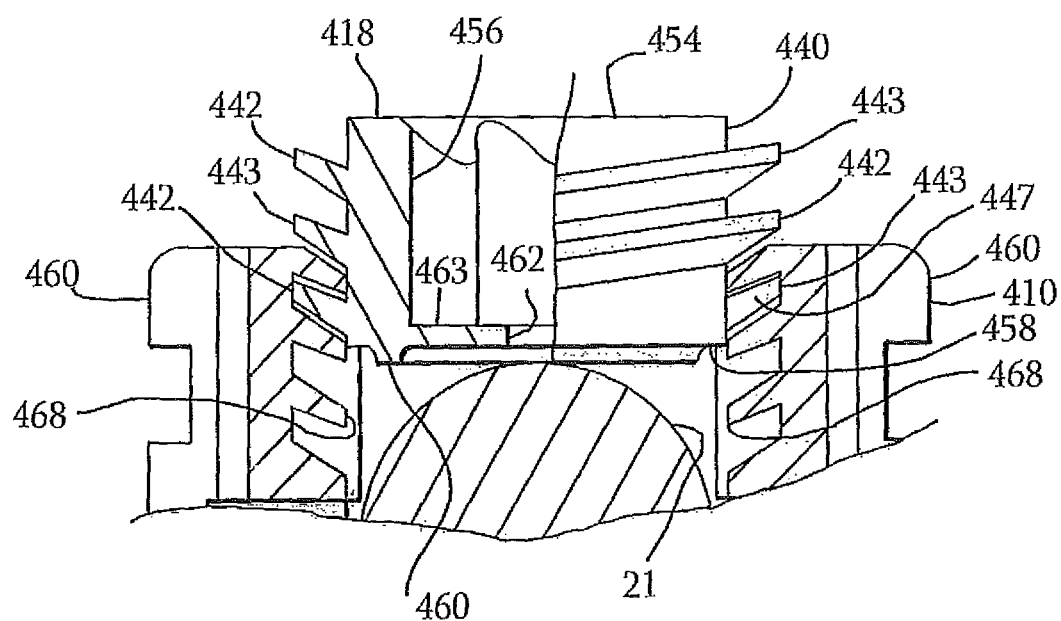
FIG. 12 is a front elevational view of an alternative reverse angle closure of an embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 12, an alternative multi-start closure top 418 is shown that is almost identical to the closure top 18 with the exception that the two flange forms 42 and 43 with respective starts 46 and 47 have been replaced with reverse angle threads 442 and 443 with respective starts 446 (not shown) and 447. Otherwise, the dual or double start closure top 418 includes a body 440, a body top surface 454, a body internal drive 456, a base 458, a rim 460', a cannulation bore 462 and a drive base surface 463 that is the same or substantially similar to the respective body 40, body top surface 54, internal drive 56, base 58, rim 60, cannulation bore 62 and drive base surface 63 previously described herein with respect to the closure top 18. The closure top 418 is shown partially wound into a polyaxial bone screw receiver 410 having opposed arms 460 with inner surfaces equipped with guide and advancement structures 468 that are sized and shaped to simultaneously closely receive and mate with the reverse angle threads 442 and 443 of the double start closure structure 418. Otherwise, the receiver 410 is identical or substantially similar to the receiver 10 described in detail in the '746 application incorporated by reference herein.

Figure 13:
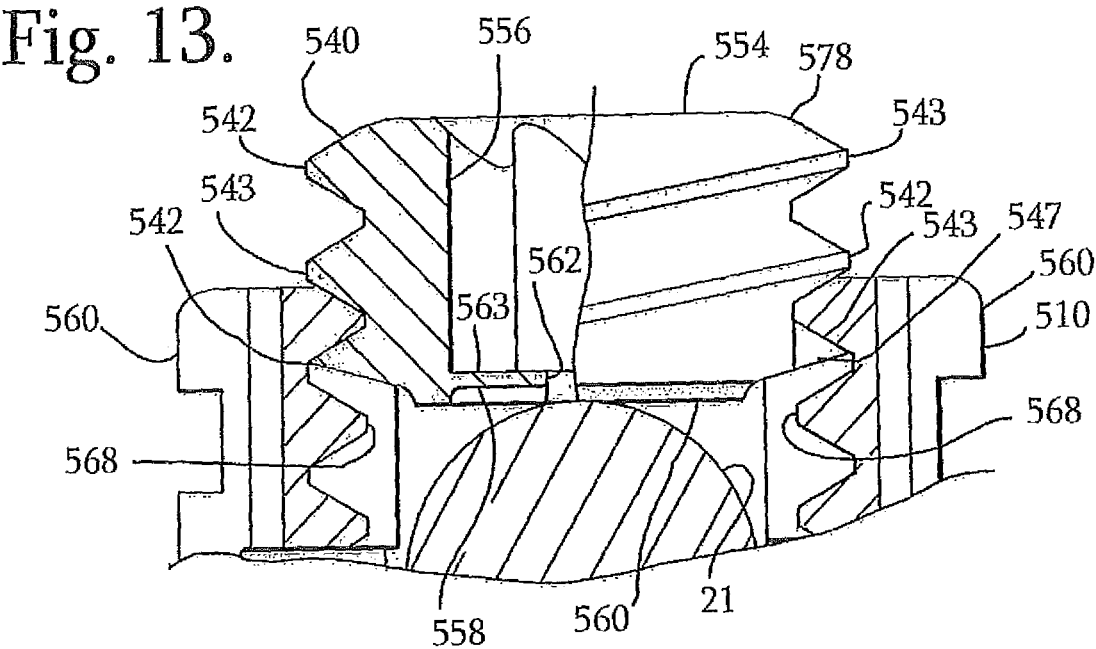
FIG. 13 is a front elevational view of an alternative v-thread closure embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 13, another alternative multi-start closure top 518 is shown that is almost identical to the closure top 18 with the exception that the two flange forms 42 and 43 with respective starts 46 and 47 have been replaced with v-threads 542 and 543 with respective starts 546 (not shown) and 547. Otherwise, the dual or double start closure top 518 includes a body 540, a body top surface 554, a body internal drive 556, a base 558, a rim 560', a cannulation bore 562 and a drive base surface 563 that is the same or substantially similar to the respective body 40, body top surface 54, internal drive 56, base 58, rim 60, cannulation bore 62 and drive base surface 63 previously described herein with respect to the closure top 18. The closure top 518 is shown partially wound into a polyaxial bone screw receiver 510 having opposed arms 560 with inner surfaces equipped with guide and advancement structures 568 that are sized and shaped to simultaneously closely receive and mate with the threads 542 and 543 of the double start closure structure 518. Otherwise, the receiver 510 is identical or substantially similar to the receiver 10 described in detail in the '746 application incorporated by reference herein.

Figure 14:
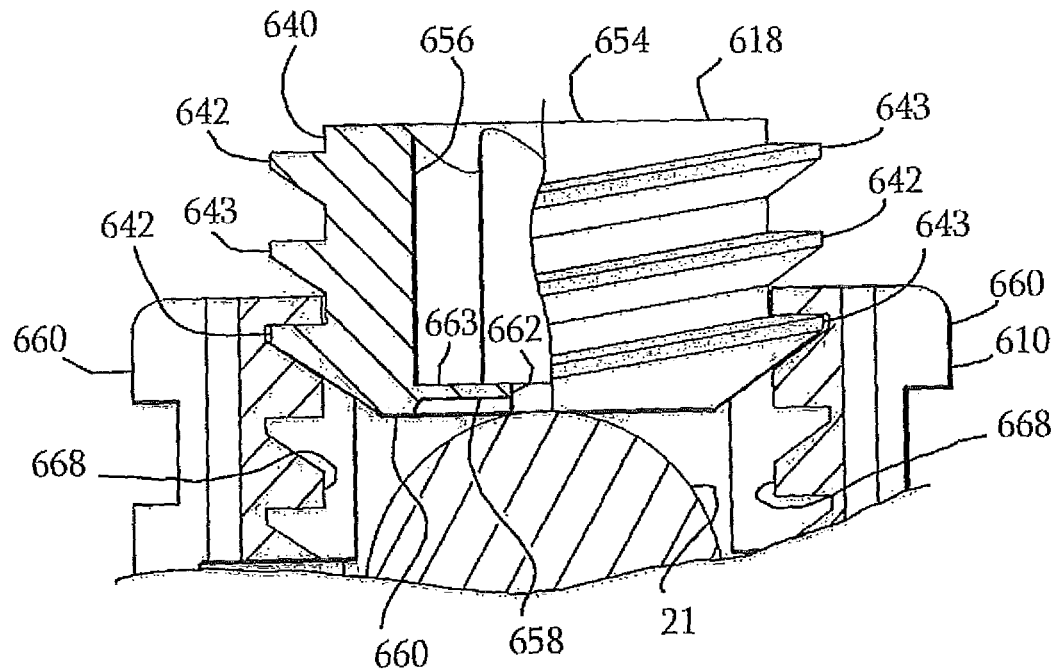
FIG. 14 is a front elevational view of an alternative buttress-thread closure embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 14, another alternative multi-start closure top 618 is shown that is almost identical to the closure top 18 with the exception that the two flange forms 42 and 43 with respective starts 46 and 47 have been replaced with buttress threads 642 and 643 with respective starts 446 and 447 (not shown). Otherwise, the dual or double start closure top 618 includes a body 640, a body top surface 654, a body internal drive 656, a base 658, a rim 660', a cannulation bore 662 and a drive base surface 663 that is the same or substantially similar to the respective body 40, body top surface 54, internal drive 56, base 58, rim 60, cannulation bore 62 and drive base surface 63 previously described herein with respect to the closure top 18. The closure top 618 is shown partially wound into a polyaxial bone screw receiver 610 having opposed arms 660 with inner surfaces equipped with guide and advancement structures 668 that are sized and shaped to simultaneously closely receive and mate with the buttress threads 642 and 643 of the double start closure structure 618. Otherwise, the receiver 610 is identical or substantially similar to the receiver 10 described in detail in the '746 application incorporated by reference herein.

With reference to FIGS. 15 and 16, an open receiver 710 is illustrated that is substantially similar to the receiver 10 previously described herein with the exception that the receiver 710 includes opposed arms 760, each having an integral upstanding break-off extension 761. Each receiver arm 760 and integral extension 761 has an inner helically wound guide and advancement structure 768 that is sized and shaped to mate with the flange forms 42 and 43 of the dual start closure 18 previously described herein. The break-off extensions 761 are initially integral with the respective arms 760 and are then broken off by a user after the closure 18 has been rotatingly advanced along the arm extensions 761 and into the channel located between the receiver arms 760. In the illustrated embodiment, in addition to an outer groove or notch 770 located at or near a top surface 769 of each of the arms 760 where the extensions 761 break off from the receiver arms, illustrated inner arm surfaces include a recess or cut 771, best shown in FIG. 16, that runs substantially horizontally. Each recess 771 is curved and elongate and disposed somewhat cross-wise or transverse to the respective flange form 768. For example, with reference to the arm 760 shown in FIG. 16, the recess 771 cuts into a weakened region, generally 780, where the arm 760 joins with the respective attached adjacent extension 761, the curved and elongate recess 771 beginning at a lower portion or location 781 of the flange form recess or segment and terminating at an opposed upper end location of the flange form segment, while otherwise leaving the flange form 768 intact. Stated in another way, the substantially horizontally extending recess 771 cuts into both a lead portion and a trailing portion of each of the flange form segments located near and directly above the opposed arms 760 and substantially opposite the notch 770, thus further weakening the region where the extension and the arm attach, without destroying the flange form path, so that the closure 18 is not derailed by the recess 771 or otherwise prohibited from moving downwardly into the receiver channel formed between the receiver arms 760.

With reference to FIG. 17, the multi-start closure 18 is shown cooperating with a spinal implant receiver, such as a bone screw receiver 10' and a discrete, detachable guide tool

801. The elongate guide tool 801, only partially shown in FIG. 17, is typically sized for extending from the bone screw receiver 10' upwardly to a location outside of a patient, the tool providing a guide channel for operably guiding the rod 21 or other longitudinal connecting member from a position exterior of the bone screw receiver 10' toward and into the bone screw receiver 10'. The illustrated guide tool has opposed arms 805, each arm having a helical guide and advancement structure 810 thereon that is illustrated as a square thread form, but may be of other geometry, including a flange form the same or similar to the flange forms 168' of the receiver 10' that mates with the flange forms 42 and 43 of the closure structure 18. Thus, the illustrated structures 810 are sized and shaped for receiving and rotating engagement with a dual start closure. The closure 18 is shown partially wound into the receiver 10' that is identical or substantially similar to the receiver 10 with the exception of certain outer arm surface features (not shown). Thus, the receiver 10' includes opposed arms 160' with inner surfaces having guide and advancement structures 168' that are sized and shaped to simultaneously closely receive and mate with the flange forms 42 and 43 of the dual start closure structure 18. The guide tool 801 includes attachment structure for detachable attachment to the receiver 10'(not shown), that may take a variety of forms and methods, including, but not limited to a slide-on, slide-off attachment, a snap-on, rotate off attachment, a rotate-on and rotate-off attachment, to name a few. For example, cooperating attachment structure for both the tool and the receiver may be used that is disclosed in U.S. Pat. No. 7,470,279 and incorporated by reference herein. Returning to the inner helically wound guide and advancement structure 810 formed on each arm 804 of the guide tool 801, the structure 810 is sized and shaped for being aligned with the receiver arms 160' during removable attachment of the tool 801 with the respective bone screw receiver 10' so as to continue the helical pathway for the closure 18, the structures 810 being synchronized with the flange forms 168' to allow for the rotation and driving transfer of the closure 18 from the tool 801 into the receiver 10'.

It is to be understood that while certain forms of the present invention have been illustrated and described herein, it is not to be limited to the specific forms or arrangement of parts described and shown.

What is claimed and desired to be secured by Letters Patent is as follows:

1. In a medical implant having a substantially cylindrical closure member and a receiver member having a first arm spaced from a second arm forming an open channel, the closure member having an axis of rotation for closing the open channel, an improvement comprising:
    a) first and second helically wound v-thread forms located on the closure member, the first helically wound v-thread form having a first start and the second helically wound v-thread form having a second start; and
    b) a first helically wound v-thread form on the first arm of the receiver member and a second helically wound v-thread form on the second arm of the receiver member opposite the first helically wound v-thread form and wherein simultaneous mating of the first start with the first helically wound v-thread form of the first arm and the second start with the second helically wound v-thread form of the first arm of the second arm occurs when the closure member is rotated between the first and second arms of the receiver member.

2. The improvement of claim 1, wherein the closure member has a break-off head.

3. The improvement of claim 1, wherein the receiver member has break-off extensions.

4. The improvement of claim 1, further comprising a guide tool having third and fourth arms detachably attached to the receiver member, the guide tool having a third discontinuous helically wound structure on the guide tool third arm and a fourth discontinuous helically wound structure on the guide tool fourth arm and wherein simultaneous mating of the first start with the third helically wound structure and the second start with the fourth helically wound structure occurs when the closure member is rotated between the third and fourth arms of the guide tool, the guide tool third and fourth helically wound structures sized and shaped to provide transfer of the closure member between the guide tool and the bone screw upon rotation of the closure member.

5. In a medical implant having a substantially cylindrical closure member and a receiver member having a first arm spaced from a second arm forming an open channel, the closure member having an axis of rotation for closing the open channel, an improvement comprising:
    a) first and second helically wound square thread forms located on the closure member, the first helically wound square thread form having a first start and the second helically wound square thread form having a second start; and
    b) a first helically wound square thread form on the first arm of the receiver member and a second helically wound square thread form on the second arm of the receiver member opposite the first helically wound square thread form and wherein simultaneous mating of the first start with the first helically wound square thread form of the first arm and the second start with the second helically wound square thread form of the second arm occurs when the closure member is rotated between the first and second arms of the receiver member.

6. The improvement of claim 5, wherein the closure member has a break-off head.

7. The improvement of claim 5, wherein the receiver member has break-off extensions.

8. The improvement of claim 5, further comprising a guide tool having third and fourth arms detachably attached to the receiver member, the guide tool having a third discontinuous helically wound structure on the guide tool third arm and a fourth discontinuous helically wound structure on the guide tool fourth arm and wherein simultaneous mating of the first start with the third helically wound structure and the second start with the fourth helically wound structure occurs when the closure member is rotated between the third and fourth arms of the guide tool, the guide tool third and fourth helically wound structures sized and shaped to provide transfer of the closure member between the guide tool and the bone screw upon rotation of the closure member.

9. In a medical implant having a substantially cylindrical closure member and a receiver member having a first arm spaced from a second arm forming an open channel, the closure member having an axis of rotation for closing the open channel, an improvement comprising:
    a) first and second helically wound reverse angle thread forms located on the closure member, the first helically wound reverse angle thread form having a first start and the second helically wound reverse angle thread form having a second start; and
    b) a first helically wound reverse angle thread form on the first arm of the receiver member and a second helically wound reverse angle thread form on the second arm of the receiver member opposite the first helically wound reverse angle thread form and wherein simultaneous mating of the first start with the first helically wound reverse angle thread form of the first arm and the second start with the second helically wound reverse angle thread form of the second arm occurs when the closure member is rotated between the first and second arms of the receiver member.

10. The improvement of claim 9, wherein the closure member has a break-off head.

11. The improvement of claim 9, wherein the receiver member has break-off extensions.

12. The improvement of claim 9, further comprising a guide tool having third and fourth arms detachably attached to the receiver member, the guide tool having a third discontinuous helically wound structure on the guide tool third arm and a fourth discontinuous helically wound structure on the guide tool fourth arm and wherein simultaneous mating of the first start with the third helically wound structure and the second start with the fourth helically wound structure occurs when the closure member is rotated between the third and fourth arms of the guide tool, the guide tool third and fourth helically wound structures sized and shaped to provide transfer of the closure member between the guide tool and the bone screw upon rotation of the closure member.

13. In a medical implant having a substantially cylindrical closure member and a receiver member having a first arm spaced from a second arm forming an open channel, the closure member having an axis of rotation for closing the open channel, an improvement comprising:
  a) first and second helically wound buttress thread forms located on the closure member, the first helically wound buttress thread form having a first start and the second helically wound buttress thread form having a second start; and
  b) a first helically wound buttress thread form on the first arm of the receiver member and a second helically wound buttress thread form on the second arm of the receiver member opposite the first helically wound buttress thread form and wherein simultaneous mating of the first start with the first helically wound buttress thread form of the first arm and the second start with the second helically wound v-thread form of the first arm of the second arm occurs when the closure member is rotated between the first and second arms of the receiver member.

14. The improvement of claim 13, wherein the closure member has a break-off head.

15. The improvement of claim 13, wherein the receiver member has break-off extensions.

16. The improvement of claim 13, further comprising a guide tool having third and fourth arms detachably attached to the receiver member, the guide tool having a third discontinuous helically wound structure on the guide tool third arm and a fourth discontinuous helically wound structure on the guide tool fourth arm and wherein simultaneous mating of the first start with the third helically wound structure and the second start with the fourth helically wound structure occurs when the closure member is rotated between the third and fourth arms of the guide tool, the guide tool third and fourth helically wound structures sized and shaped to provide transfer of the closure member between the guide tool and the bone screw upon rotation of the closure member.

17. A medical implant comprising:
  a) a receiver having a body and a pair of upstanding spaced arms forming a channel for receiving a longitudinal connecting member, each arm having an inwardly facing surface with a first helically wound guide and advancement structure located thereon; and
  b) a closure structure having a cylindrical body and a second helically wound guide and advancement structure including at least two v-threads and having at least two starts.

18. The implant of claim 17, wherein the closure structure has a break-off head.

19. The implant of claim 17, wherein the receiver has break-off extensions.

20. A medical implant comprising:
  a) a receiver having a body and a pair of upstanding spaced arms forming a channel for receiving a longitudinal connecting member, each arm having an inwardly facing surface with a first helically wound guide and advancement structure located thereon; and
  b) a closure structure having a cylindrical body and a second helically wound guide and advancement structure including at least two square threads and having at least two starts.

21. The implant of claim 20, wherein the closure structure has a break-off head.

22. The implant of claim 20, wherein the receiver has break-off extensions.

23. A medical implant comprising:
  a) a receiver having a body and a pair of upstanding spaced arms forming a channel for receiving a longitudinal connecting member, each arm having an inwardly facing surface with a first helically wound guide and advancement structure located thereon; and
  b) a closure structure having a cylindrical body and a second helically wound guide and advancement structure including at least two reverse angle threads and having at least two starts.

24. The implant of claim 23, wherein the closure structure has a break-off head.

25. The implant of claim 23, wherein the receiver has break-off extensions.

26. A medical implant comprising:
  a) a receiver having a body and a pair of upstanding spaced arms forming a channel for receiving a longitudinal connecting member, each arm having an inwardly facing surface with a first helically wound guide and advancement structure located thereon; and
  b) a closure structure having a cylindrical body and a second helically wound guide and advancement structure including at least two buttress threads and having at least two starts.

27. The implant of claim 26, wherein the closure structure has a break-off head.

28. The implant of claim 26, wherein the receiver has break-off extensions.

29. A medical implant comprising:
  a) a receiver having a body with a channel for receiving a longitudinal connecting member, the receiver having a first receiver helically wound thread form and a second receiver helically wound thread form; and
  b) a closure having a cylindrical body including a first closure helically wound thread form and a second closure helically wound thread form, the first closure helically wound thread form including a first start and the second closure helically wound thread form including a second start, the first and second receiver helically wound thread forms and the first and second closure helically wound thread forms being at least one of buttress thread forms, reverse angle thread forms, v-thread forms, or square thread forms, the first and second receiver helically wound thread forms mating with the first and second closure helically wound thread forms when the closure is rotated with respect to the receiver.

30. A medical implant having a cylindrical closure and a receiver, the receiver having a longitudinal connecting member receiving channel, the closure having an axis of rotation for being rotationally advanced into a central opening on a top of the receiver, the medical implant comprising:
- a first closure helically wound reverse angle thread form on the closure having a first start;
- a second closure helically wound reverse angle thread form on the closure having a second start;
- a first receiver helically wound reverse angle thread form in the central opening of the receiver; and
- a second receiver helically wound reverse angle thread form opposite the first receiver helically wound reverse angle thread form in the central opening of the receiver, the first and second closure helically wound thread forms mating with the first and second receiver closure thread forms when the closure is rotated with respect to the receiver.

* * * * *